US00PP31879P2

(12) United States Plant Patent
Danziger

(10) Patent No.: US PP31,879 P2
(45) Date of Patent: Jun. 16, 2020

(54) ***VERBENA* PLANT NAMED 'DVERVAVL'**

(50) Latin Name: ***Verbena* hybrid**
Varietal Denomination: DVERVAVL

(71) Applicant: Gavriel Danziger, Beit Dagan (IL)

(72) Inventor: Gavriel Danziger, Beit Dagan (IL)

(73) Assignee: Danziger 'DAN' Flower Farm (IL)

( * ) Notice: Subject to any disclaimer, the term of this patent is extended or adjusted under 35 U.S.C. 154(b) by 0 days.

(21) Appl. No.: 16/501,629

(22) Filed: May 14, 2019

(51) Int. Cl.
*A01H 5/02* (2018.01)
*A01H 6/86* (2018.01)

(52) U.S. Cl.
USPC ..... Plt./308

(58) Field of Classification Search
USPC ..... Plt./308
See application file for complete search history.

*Primary Examiner* — Susan McCormick Ewoldt
(74) *Attorney, Agent, or Firm* — Cassandra Bright

(57) ABSTRACT

A new and distinct *Verbena* cultivar named 'DVERVAVL' is disclosed, characterized by early flowering, an abundance of magenta flowers, semi-trailing habit and tolerance to powdery mildew. The new variety is a *Verbena*, normally produced as an outdoor garden or container plant.

2 Drawing Sheets

Figure 1:
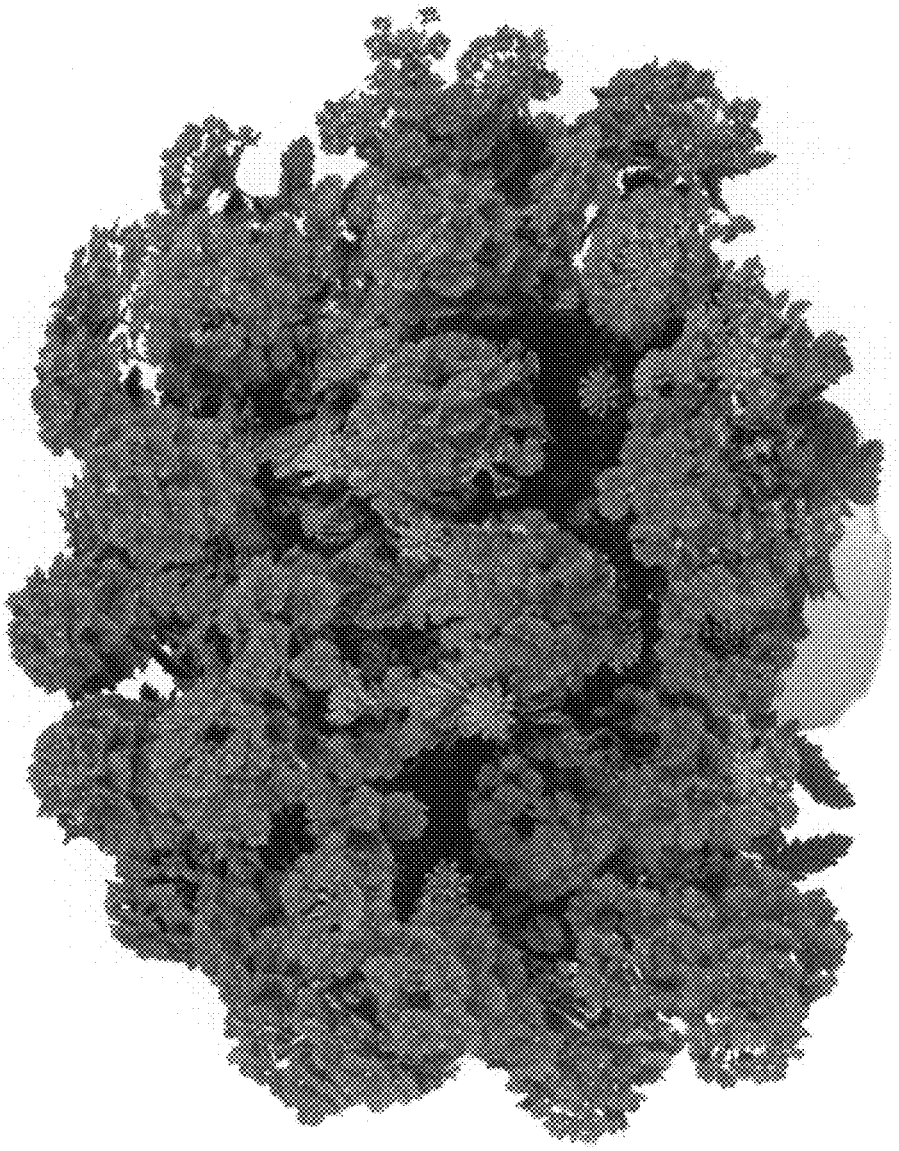

Latin name of the genus and species: *Verbena* hybrid.
Variety denomination: 'DVERVAVL'.

BACKGROUND OF THE INVENTION

The new *Verbena* cultivar is a product of a planned breeding program conducted by the inventor, Gavriel Danziger in Moshav Mishmar Hashiva, Israel. The objective of the breeding program was to produce new *Verbena* varieties for ornamental purposes. The cross resulting in this new variety was made during January of 2015.

The seed parent is the, unpatented, propriety variety referred to as *Verbena* 'VE-14-7534'. The pollen parent is the, unpatented, propriety variety referred to as *Verbena* 'VE-15-8069'. The new variety was discovered in September of 2015 by the inventor in a group of seedlings resulting from the crossing, in a greenhouse in Moshav Mishmar Hashiva, Israel. Date of first sale was Jun. 3, 2018, in Israel. This sale was made directly by the inventor or one who obtained the claimed invention directly or indirectly from the inventor. This sale and all public disclosures made between Jun. 3, 2018, and the filing of this application fall within the exception allowed under 102(b)(1).

Asexual reproduction of the new cultivar 'DVERVAVL' first by vegetative terminal cuttings was first performed during September of 2015, at a greenhouse in Moshav Mishmar Hashiva, Israel. Subsequent propagation by vegetative cuttings has shown that the unique features of this cultivar are stable and reproduced true to type in multiple successive generations.

SUMMARY OF THE INVENTION

The cultivar 'DVERVAVL' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DVERVAVL' These characteristics in combination distinguish 'DVERVAVL' as a new and distinct *Verbena* cultivar:

1. Flowers early.
2. Semi-trailing habit.
3. Tolerant to powdery mildew.
4. Highly floriferous plants.
5. Bright magenta flower color.

PARENT COMPARISON

Plants of the new cultivar 'DVERVAVL' are similar to plants of the seed parent in most horticultural characteristics, however, plants of the new cultivar 'DVERVAVL' differ in the following;

1. New variety is more vigorous than the seed parent, which has weaker growing habit.
2. The flower color of the new variety is darker than the parent.

Plants of the new cultivar 'DVERVAVL' are similar to plants of the pollen parent in most horticultural characteristics, however, plants of the new cultivar 'DVERVAVL' differ in the following;

1. The new variety has a lighter flower color than the parent.
2. The new variety is more tolerant to powdery mildew than the parent.
3. The new variety has a semi-trailing habit, while the parent is compact and mounding.

COMMERCIAL COMPARISON

Plants of the new cultivar 'DVERVAVL' can be compared to the unpatented commercial variety *Verbena* 'Estrella Up Blueberry'. These varieties are similar in most horticultural characteristics; however, 'DVERVAVL' differs in the following:

1. The new variety has a darker flower color than this comparator.
2. The new variety is more tolerant to powdery mildew than this comparator.

Plants of the new cultivar 'DVERVAVL' can also be compared to the unpatented commercial variety *Verbena* 'EnduraScape Blue'. These varieties are similar in most horticultural characteristics; however, 'DVERVAVL' differs in the following:

1. The new variety has a darker flower color than this comparator.
2. The new variety has a semi-trailing habit, while this comparator has a trailing habit.
3. The new variety has larger flowers than this comparator.

BRIEF DESCRIPTION OF THE PHOTOGRAPHS

The accompanying photograph in FIG. 1 illustrates in full color a typical plant of 'DVERVAVL' grown in in a greenhouse, in Moshav Mishmar Hashiva, Israel, photographed in February.

Figure 2:
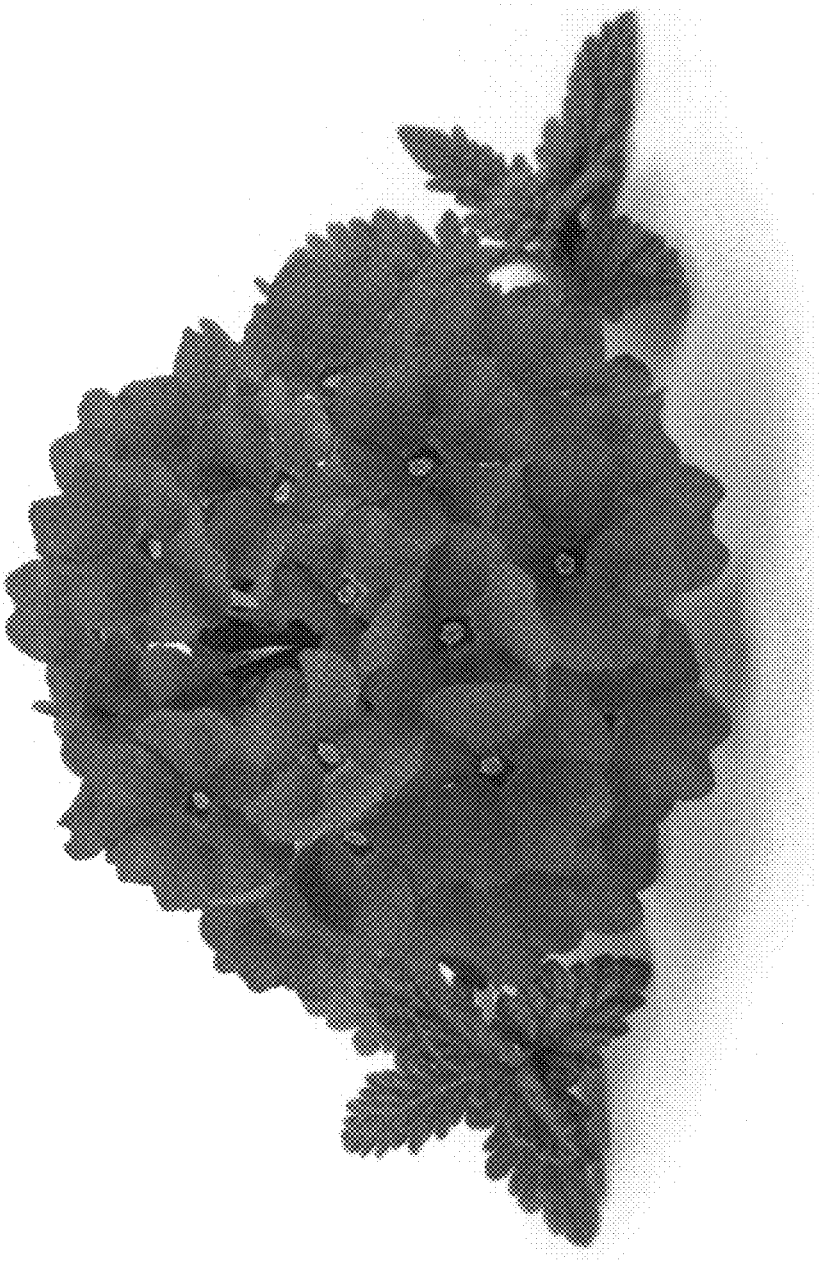

FIG. 2 illustrates in full color a typical inflorescence of 'DVERVAVL'. Age of the plant photographed is approximately 20 weeks from a rooted cutting in a 20 cm pot.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DVERVAVL' plants grown in a nursery in Moshav Mishmar Hashiva, Israel, under natural lighting. Measurements were taken during March of 2019. The plants were approximately 80 days from a rooted cutting in a 12 cm pot. The growing temperature ranged from 18° C. to 27° C. during the days, 10° C. to 15° C. during the nights. Measurements and numerical values represent averages of typical plant types.

Botanical classification: *Verbena* hybrid 'DVERVAVL'.

PROPAGATION

Time to initiate roots: 7 to 9 days at optimal temperature of approximately 23° C.

Root description: Fibrous. Brown, not accurately measured with a color chart.

PLANT

Growth habit: Semi-trailing.
Pot size of plant described: 12 cm.
Height: 12 cm.
Plant spread: 35 cm.
Growth rate: Fast.
Branching characteristics: Freely branching.
Length of primary lateral branches: 23 cm.
Diameter of lateral branches: 0.4 cm.
Quantity of primary lateral branches: Approximately 8.
Characteristics of primary lateral branches:
- *Form*.—Cylindrical.
- *Diameter*.—0.3 cm.
- *Color*.—Near Yellow-Green 144B.
- *Texture*.—Pubescent.
- *Strength*.—Flexible.

Internode length: 2 cm.

FOLIAGE

Leaf:
- *Arrangement*.—Opposite.
- *Quantity*.—Approximately 20 per branch.
- *Average length*.—4 cm.
- *Average width*.—2.5 cm.
- *Shape of blade*.—Triangular.
- *Apex*.—Acute.
- *Base*.—Acute.
- *Margin*.—Serrate.
- *Texture of top surface*.—Pubescent.
- *Texture of bottom surface*.—Pubescent.
- *Pubescence*.—Strigose.
- *Aspect*.—45 degrees.
- *Color*.—Young foliage upper side: RHS Green 137C. Young foliage under side: RHS Green 138B. Mature foliage upper side: RHS Green N137A. Mature foliage under side: RHS Green 137D.
- *Venation*.—Type: Pinnate. Venation color upper side: RHS Green 139C. Venation color under side: RHS Green 139D.
- *Petiole*.—Length: 0.5 cm. Diameter: 0.1 cm. Color: RHS Green 137A. Texture: Pubescent.

FLOWER

Natural flowering season: Spring to Autumn.
Days to flowering from rooted cutting: 45 to 50 days.
Inflorescence and flower type and habit: Terminal cluster.
Rate of flower opening: 4 to 6 days from bud to fully opened flower.
Flower longevity on plant: 5 to 8 days.
Persistent or self-cleaning: Self-cleaning.

Bud:
- *Shape*.—Quinquangular.
- *Length*.—1 cm.
- *Diameter*.—0.2 cm.
- *Color*.—RHS Green 139D.

Corolla:
- *Flower*.—Depth: 1 cm. Diameter: 0.2 cm. Petals/lobes: Number: 5. Length: 1 cm. Width: 1 cm. Shape: Obcordate. Aspect: Upright. Margin: Entire. Texture: Smooth.
- *Color*.—When opening: Upper surface: RHS Red-Purple 72A. Lower surface: RHS Red-Purple 76A. Fully opened: Upper surface: RHS Purple N78A. Lower surface: RHS Violet 85C. Throat: Color: RHS White NN155A. Texture: Smooth. Tube color: RHS White NN155A.

Calyx:
- *Form*.—Tubular.
- *Length*.—1.3 cm.
- *Diameter*.—0.2 cm.
- *Sepal shape*.—Five sepals whose margins are fused-quinquangular.
- *Sepal margin*.—Entire.
- *Sepal texture*.—Pubescent.
- *Sepal color*.—Upper surface: RHS Yellow-Green 144B. Lower surface: RHS Yellow-Green 144B.

Pedicels: None.
Fragrance: None.

REPRODUCTIVE ORGANS

Stamens:

*Number* (*per flower*).—4.

*Filament length*.—0.2 cm.

*Anthers*.—Shape: Conical. Length: 0.1 cm. Color: RHS Yellow-Green 154B.

Pollen: None.

Pistils:

*Quantity per flower*.—1.

*Length*.—0.8 cm.

*Styles*.—Length: 0.8 cm.

*Color*.—RHS Green-Yellow 1C.

*Stigma*.—Shape: Ovoid. Color: RHS Yellow-Green 144A.

OTHER CHARACTERISTICS

Seeds and fruits: Scant seeds. Seeds colored near Grey-Brown 199A, near 1 mm long and 0.3 in diameter.

Disease/pest resistance: Tolerant to powdery mildew (*Erysiphe cichoracearum*). Neither resistance nor susceptibility to other diseases and pests of *Verbena* observed.

Temperature tolerance: Tolerates temperatures from approximately −1° C. to 32° C.

What is claimed is:

1. A new and distinct cultivar of *Verbena* plant named 'DVERVAVL' as herein illustrated and described.

* * * * *